(12) United States Patent
Bertrand et al.

(10) Patent No.: US 6,222,032 B1
(45) Date of Patent: Apr. 24, 2001

(54) USE OF YLIDES OF PHOSPHORUS AS SLIGHTLY NUCEOPHILIC STRONG BASES

(75) Inventors: Guy Bertrand, Pechbusque; Dennis Bigg, Gif-sur-Yvette; Jean-Bernard Cazaux, Aramon; Stéphanie Goumri, Toulouse; Olivier Guerret, Marcy l'Etoile, all of (FR)

(73) Assignees: Societe de Conseils de Recherches d'Applications Scientifiques (SCRAS); Centre National de la Recherche Scientifique (CNRS), both of (FR)

( * ) Notice: Subject to any disclaimer, the term of this patent is extended or adjusted under 35 U.S.C. 154(b) by 0 days.

(21) Appl. No.: 09/423,269
(22) PCT Filed: May 26, 1998
(86) PCT No.: PCT/FR98/01048
   § 371 Date: Nov. 4, 1999
   § 102(e) Date: Nov. 4, 1999
(87) PCT Pub. No.: WO98/54229
   PCT Pub. Date: Dec. 3, 1998

(30) Foreign Application Priority Data

May 26, 1997 (EP) .................................................. 97401142

(51) Int. Cl.$^7$ ...................... C07D 243/16; C07D 207/12; C07F 9/02
(52) U.S. Cl. ............................ 540/504; 548/543; 564/12; 564/14; 558/177; 558/183; 558/185
(58) Field of Search ............................... 564/12, 14, 177; 558/177, 183, 185; 548/543; 540/504

(56) References Cited

U.S. PATENT DOCUMENTS

| | | |
|---|---|---|
| 3,274,228 | 9/1966 | Pappas et al. . |
| 3,681,428 | 8/1972 | Roberts et al. . |
| 3,725,365 | 4/1973 | McKinley et al. . |
| 3,919,126 | 11/1975 | Rakshys, Jr. et al. . |
| 4,043,948 | 8/1977 | Rakshys, Jr. et al. . |
| 4,092,466 | * 5/1978 | Fletcher et al. ........................ 526/13 |

FOREIGN PATENT DOCUMENTS

| | | |
|---|---|---|
| 2022489 | 1/1971 | (DE) . |
| 0030516 | 6/1981 | (EP) . |
| 0744393 | 11/1996 | (EP) . |
| 2019198 | 6/1970 | (FR) . |

OTHER PUBLICATIONS

Hawley's "Condensed Chemical Dictionary" 12th edition, Editor Richard J Lewis Sr., Van Nostrand Reinhold publisher, New York 1993.*

CA:132:264725 abs of Tetrahedron by Palacios et al 56(4) pp 663–669 2000.*

CA:126:225346 abs of J Org Chem by Reynolds et al 62(8) pp 2574–2593 1997.*

CA:108:221796 abs of J Am Chem Soc by Vedejs et al 110(12) pp3940–8 1988.*

* cited by examiner

Primary Examiner—Jean F. Vollano
(74) Attorney, Agent, or Firm—Bierman, Muserlian and Lucas

(57) ABSTRACT

In a process for C-alkylation or N-alkylation, the improvement comprising conducting the C-alkylation or N-alkylation reaction in the presence of a slightly nucleophilic strong base of the following formula

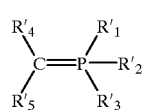

I' wherein $R'_1$, $R'_2$ and $R'_3$ are individually selected from the group consisting of alkoxy of 1 to 6 carbon atoms and

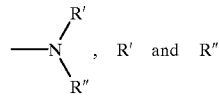

, R' and R''

R' and R'' are individually selected from the group consisting of unsubstituted or substituted alkyl of 1 to 6 carbon atoms, alkoxy of 1 to 6 carbon atoms, cycloalkyl of 3 to 10 carbon atoms, aryl and aralkyl of 1 to 6 alkyl carbon atoms, the substituents being selected from the group consisting of halogen, alkyl of 1 to 6 carbon atoms, alkoxy of 1 to 6 carbon atoms, —CN, —NO$_2$ and dialkylamino of 1 to 6 alkyl carbon atoms, the aryl being selected from the group consisting of unsaturated monocyclic and condensed carbocyclic and heterocyclic with at least one heteroatom selected from the group consisting of nitrogen, oxygen and sulfur, $R'_4$ is selected from the group consisting of hydrogen, alkyl of 1 to 6 carbon atoms and alkoxy of 1 to 6 carbon atoms and $R'_5$ is selected from the group consisting of hydrogen, alkyl of 1 to 6 carbon atoms, alkoxy of 1 to 6 carbon atoms and a polymeric support.

22 Claims, No Drawings

USE OF YLIDES OF PHOSPHORUS AS SLIGHTLY NUCEOPHILIC STRONG BASES

This application is a 371 of PCT Application No. FR98/01048 filed on May 26, 1998, now WO 98/54229.

The present invention relates to the use of phosphorus ylides as slightly nucleophilic strong bases. The invention also relates to new phosphorus ylides and their preparation.

Strong organic bases are generally necessary to functionalize organic or organometallic molecules; and the stronger the base, the better it traps the protons. In order to limit parasitic reactions, it is preferable and even desirable to choose a base which is only slightly nucleophilic. Moreover, the ease with which the acid obtained is separated from the reaction medium is a determinant factor in order to simplify the purification stages.

Phosphorus ylides were studied by Wittig in the 1950's (Johnson, A. W., 1993, Series, Editor, *Ylides and Imines of phosphorus*, Wiley & Wiley: New York). These molecules are quite simple and even if some are presented as colorants (U.S. Pat. No. 3,274,228), they are usually prepared to be used for Wittig's reaction (U.S. Pat. Nos. 3,681,428, 3,725,365) where their strong nucleophilic action is involved. But these compounds have never been used as bases in organic synthesis, and a fortiori as slightly nucleophilic strong bases.

The strong neutral organic bases known to date are essentially proton sponges (Alder, R. et al., *J. Chem. Soc. Chem. Commun.*, 1968, 723), guanidines, phosphatranes and polyphosphazenes.

Guanidines constitute the class of strong organic bases most frequently used in organic synthesis. The best known are DBN (1,5-diazabicyclo [4.3.0] non-5-ene) and DBU (1,8-diazabicyclo [4.3.0] undec-5-ene). Other guanidines are also mentioned in the literature (Oediger, H. et al., *Synthesis*, 1972, 593; Schwesinger, R., *Angew. Chem. Int. Ed. Eng.*, 1987, 26, 1164). These bases are used in elimination reactions or in oligomerization or polymerization processes as a reaction initiator (Oediger, H. et al., *Synthesis*, 1972, 593; Wöhrle, D. et al., *Dyes and Pigments*, 1992, 18, 91).

Phosphatranes are more recent compounds (Verkade, J., 1991, *Phosphatranes as proton abstracting reagents*, U.S. Pat. No. 5,051,533). Their basicity is much greater than that of guanidines, which extends their field of application. The drawback of such phosphines lies in the difficulty in obtaining them and their purification.

As regards polyphosphazenes, recently developed by Schwesinger, these are the most basic organic molecules demonstrating a very slight nucleophilic action. They are however very difficult to synthesize and their cost is very high (Schwesinger, R. et al., *Liebigs Ann.*, 1996, 1055; Schwesinger, R. et al., *Angew. Chem. Int. Ed. Engl.*, 1991, 30, 1372; Schwesinger, R. et al., *Angew. Chem. Int. Ed. Engl.*, 1987, 26, 1167; Schwesinger, R. et al., *Angew. Chem. Int. Ed. Engl.*, 1987, 26, 1165; Schwesinger, R., *Chimia*, 1985, 39, 269). Their uses are very varied: they range from simple elimination to the benzylation of oligopeptides (Schwesinger, R., *Chimia*, 1985, 39, 269; Pietzonka, T. et al., *Angew. Chem. Int. Ed. Engl.*, 1992, 31, 1481). The basicity of these molecules is sufficient to remove the slightly acidic protons and their organic character avoids the undesirable effects of salts in certain alkylations (Pietzonka, T. et al., *Chem. Ber.*, 1991, 124, 1837).

Alkaline bases such as BuLi, LiHMDS, NaHMDS, LDA also represent another large family of bases. They are often used with good yields to functionalize lactames, ketones or Schiff bases (Stork, G. et al., *J. Org. Chem.*, 1976, 41, 3491; Myers, A. et al., *J. Am. Chem. Soc.*, 1994, 116, 9361; Myers, A. et al., *J. Am. Chem. Soc.*, 1995, 117, 8488; Yaozhong, J. et al., *Synth. Commun.*, 1990, 20, 15; Butcher, J., Liverton, N., Selnick, H., Helliot, J., Smith, G., et al., *Tet. Lett.*, 1996, 37, 6685; Davis, F., Sheppard, A. et al., *J. Am. Chem. Soc.*, 1990). The effects of salts are very frequent and often vary from one reaction to another and these bases retain a strong nucleophilic character even at low temperatures. (Meyers, A., Kunnen, K., *J Am. Chem. Soc.*, 1987, 109, 4405).

The problem is therefore to find slightly nucleophilic strong bases, which are easy to synthesize and at a low cost, which would be susbstituted on the one hand for commonly used bases which are too nucleophilic and on the other hand for recent bases which are too expensive.

The invention therefore relates to the use of products of general formula I'

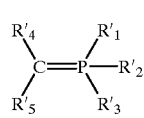

in which

R'$_1$, R'$_2$ and R'$_3$ represent, independently, a lower alkoxy or amino radical of formula R'R"N in which R' and R" independently represent one of the following radicals, non-substituted or substituted (by one or more identical or different substituents): lower alkyl, lower alkoxy, cycloalkyl, lower aryl-alkyl, aryl, in which the substituent is a halogen atom or a lower alkyl, lower alkoxy, cyano, nitro or dialkylamino radical;

R'$_4$ represents the hydrogen atom, a lower alkyl radical or lower alkoxy;

R'$_5$ represents the hydrogen atom, a lower alkyl radical, lower alkoxy or a polymeric support;

as a slightly nucleophilic strong base.

In the definitions indicated above, the expression halogen represents a fluorine, chlorine, bromine or iodine atom, preferably chlorine or bromine. The expression lower alkyl represents a linear or branched alkyl radical having 1 to 6 carbon atoms and in particular an alkyl radical having 1 to 4 carbon atoms such as the methyl, ethyl, propyl, isopropyl, butyl, isobutyl, sec-butyl and tert-butyl radicals.

The lower alkoxy radicals can correspond to the alkyl radicals indicated above. Among the linear radicals, there can be mentioned the methoxy, ethoxy, propyloxy, n-butyloxy or n-hexyloxy radicals. Among the branched alkoxy radicals, there can be mentioned the isopropyloxy, sec-butyloxy, isobutyloxy, ter-butyloxy, isopentyloxy, neo-pentyloxy or ter-pentyloxy radicals.

The term cycloalkyl includes any non-aromatic cyclic hydrocarbon fragment having 3 to 10 carbon atoms and preferably cyclopropyl, cyclobutyl, cyclopentyl or cyclohexyl.

The term aryl designates radicals which are unsaturated, monocyclic or constituted by condensed rings, carbocyclic or heterocyclic, it being understood that the heterocyclic radicals can include one or more identical or different heteroatoms chosen from oxygen, sulphur or nitrogen. Examples of such groups include the phenyl, thienyl, furyl, pyridyl, pyrimidyl, pyrrolyl, thiazolyl, isothiazolyl, diazolyl, triazolyl, thiatriazolyl, oxazolyl, benzothienyl, benzofuryl, benzopyrrolyl, benzimidazolyl, benzaxozolyl, indolyl, purinyl, naphthyl, thionaphthyl, phenanthrenyl, anthracenyl, biphenyl, indenyl, quinolyl, isoquinolyl or quinolizinyl radicals. The lower arylalkyl radicals designate the radicals in which the aryl and lower alkyl radicals respectively are as defined above such as for example benzyl, phenethyl or naphthylmethyl.

The term dialkylamino represents the amino radical substituted by two alkyl radicals, identical or different, as defined above, such as for example dimethylamino, (methyl)(ethyl)amino, diethylamino.

The expression slightly nucleophilic means non nucleophilic with respect to other centres than protons. The term strong base corresponds to the term commonly used by a person skilled in the art in the technical field considered. The polymeric support can be, for example, of methacrylic, acrylic or styrenic type.

The invention relates more particularly to the use, as a slightly nucleophilic strong base, of products of general formula I' as defined above characterized in that $R'_1$, $R'_2$ and $R'_3$ represent, independently, an amino radical of formula RR'N as defined above. Preferably, $R'_1$, $R'_2$ and $R'_3$ represent, independently, the dimethylamino, (methyl)(ethyl)amino or diethylamino radical.

The invention relates more particularly to the use, as a slightly nucleophilic strong base, of products of general formula I'as defined above characterized in that $R'_4$ represents the hydrogen atom or an alkyl radical. Preferably, $R'_4$ represents the hydrogen atom or the methyl or ethyl radical.

The invention also relates more particularly to the use, as a slightly nucleophilic strong base, of products of general formula I'as defined above characterized in that $R'_5$ represents an alkyl radical, and preferably methyl, or a polymeric support. Preferentially, the polymeric support $R'_5$ is of methacrylic type, acrylic type such as the expansine® polymer, or polystyrenic type. Preferably, the polymeric support of polystyrenic type is of general formula (s)

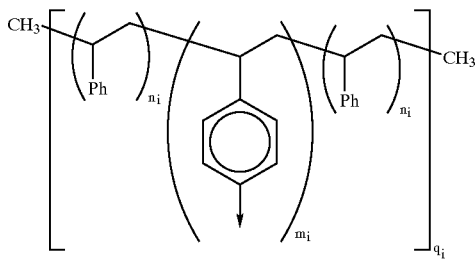

in which $n_i$, $m_i$ and $q_i$ are integers greater than or equal to one.

The polymeric support of formula (s) can originate from the corresponding polymer of formula (p)

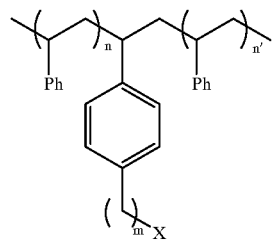

in which n, n', m are integers greater than or equal to one and X represents a parting group. As a parting group, X can be, for example, a halogen atom, the oxycarbonyl, oxysulphonyl or oxyboronyl radical. Preferably, the polymeric support $R'_5$ originates from a polystyrenic polymer of general formula (p) as defined above in which X represents the chlorine atom and m is equal to 1, and more particularly Merrifield resin.

A more particular subject of the invention is the use of the compounds of formula I' as defined above, as slightly nucleophilic strong bases in N-alkylation reactions such as, for example, the N-alkylation reactions of lactames, succinimides, oligopeptides and benzodiazepines.

A more particular subject of the invention is also the use of the products of general formula I' as defined above as slightly nucleophilic strong bases in C-alkylation reactions such as, for example, the C-alkylation reactions of lactames, succinimides, Schiff bases and benzodiazepines.

A more particular subject of the invention is the use of the products corresponding to the following formulae:
styrene/divinylbenzene-tris(dimethylamino)methylenephosphorane copolymer;
tris(dimethylamino)-C-dimethylmethylene phosphorane. as a slightly nucleophilic strong base, and in particular in N-alkylation or C-alkylation reactions.

Among the compounds of formula I' as defined, certain are known (Johnson, A. W., 1993, Series, Editor, *Ylides and Imines of phosphorus*, Wiley & Wiley: New York).

Therefore, a subject of the invention is also new phosphorus ylides and more particularly the products of general formula (I)

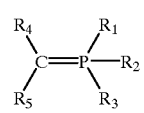

in which $R_1$, $R_2$ and $R_3$ represent, independently, a lower alkoxy or amino radical of formula R'R"N in which R' and R" independently represent one of the following radicals, non-substituted or substituted (by one or more identical or different substituents): lower alkyl, lower alkoxy, cycloalkyl, lower aryl-alkyl, aryl, in which the substituent is a halogen atom or a lower alkyl, lower alkoxy, cyano, nitro or dialkylamino radical;

$R_4$ represents the hydrogen atom, a lower alkyl or lower alkoxy radical; and $R_5$ represents a polymeric support.

A more particular subject of the invention is the products of general formula I as defined above characterized in that $R_1$, $R_2$ and $R_3$ represent, independently, an amino radical of formula RR'N as defined above. Preferably, $R_1$, $R_2$ and $R_3$ represent, independently, the radical dimethylamino, (methyl)(ethyl)amino, diethylamino radical.

A more particular subject of the invention is the products of general formula I as defined above characterized in that $R_4$ represents the hydrogen atom.

A more particular subject of the invention is the products of general formula I as defined above characterized in that the polymeric support $R_5$ is of methacrylic type, acrylic type such as the polymer expansine®, or polystyrenic type. Preferably, the polymeric support of polystyrenic type is of general formula (s) as defined above.

A subject of the invention is also a process for the preparation of the products of general formula I as defined above, characterized in that
a phosphine of general formula (1)

$$PR_1R_2R_3 \quad (1)$$

in which $R_1$, $R_2$ and $R_3$ have the meaning indicated above, is reacted with a compound of general formula (2)

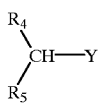
(2)

in which $R_4$ and $R_5$ have the meaning indicated above and Y is such that $Y^-$ represents any anion, in order to obtain the product of general formula (3)

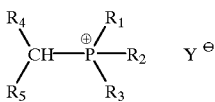
(3)

which product (3) thus obtained is treated with a strong base in order to obtain a product of formula I.

The preparation of compound (3), from compounds (1) and (2) is preferably carried out under an inert atmosphere, such as for example under an argon atmosphere, in a polar solvent such as 1,2-dichloroethane, acetonitrile, dimethoxyethane or diethoxymethane. Compound (2) is in general in stoechiometric excess with respect to compound (1). In this compound (2), Y is such that $Y^-$ represents any anion known to a person skilled in the art such as, for example, halides, triflate. The reaction medium is then agitated under reflux of the solvent. After the standard washing stages, compound (3) is dried under vacuum. In order to obtain product (I), product (3) thus obtained is treated, at ambient temperature, in the presence of a strong base. The strong base can be for example a lithiated base such as alkyl lithium compounds, and more particularly butyllithium, a sodium or potassium hydride, an amide or an alcoholate. The solvent can be chosen from pentane, ether, tetrahydrofuran, dimethoxyethane or diethoxymethane, in which solvent the strong base is stable. The mixture obtained is agitated for a few hours. Polymer (I) is washed under vacuum then dried. It can then be used directly without further purification.

The compound of formula (1) in which $R_4$ does not represent the hydrogen atom, can be obtained by reacting the corresponding compound (I) in which $R_4$ represents the hydrogen atom, with a compound of formula $R_4X'$ in which $X'$ represents a halogen atom and $R_4$ is as defined above but does not represent the hydrogen atom, at a temperature comprised between $-10$ and $+10°$ C., preferably at $0°$ C., in a solvent such as THF. After filtration and washing, the product thus obtained can be treated with a strong base in order to obtain the desired compound (I).

A subject of the invention is also, as new industrial products, and in particular as new industrial products intended for the preparation of products of formula (I), the products of formula (3) as described above.

The compounds of formula (1) and (2) are generally commercial products and can be obtained according to standard methods known to a person skilled in the art. The compounds of formula (I') in which $R'_5$ represents the hydrogen atom, a lower alkyl or lower alkoxy radical, can be prepared according to standard methods known to a person skilled in the art (Johnson, A. W., 1993, Series, Editor, *Ylides and Imines of phosphorus*, Wiley & Wiley: New York).

The following examples are presented in order to illustrate the above procedures and must in no case be considered as a limit to the scope of the invention.

EXPERIMENTAL PART

EXAMPLE 1

Preparation of a Supported Ylide

Stage 1a: Preparation of Compound (3)

7 g of Merrifield resin (1 meq/g) is placed under an inert atmosphere of argon. A solution of 21 mmol of $P(NMe_2)_3$ in 100 ml of dichloroethane is added and the reaction medium is maintained under magnetic stirring for 5 days at ambient temperature. The polymer is then washed several times with dichloromethane in order to remove the excess phosphine. It is then dried under vacuum until the polymer mass obtained does not change any more (8 g). Compound (3) is obtained in the form of a fine white sand. (M.p. (dec.): $325°$ C.).

The grafting rate is checked by the reactivity of the polymer obtained. The solvent used for the grafting can also be dimethoxyethane.

1b: Preparation of Compound (I)

1.1 mmol of butyllithium is added at ambient temperature to 1 g of compound (3) in suspension in 20 ml of tetrahydrofuran (THF). The mixture becomes red and heat is seen to be generated. Stirring is maintained for one hour. 40 ml of THF is then added and the polymer is recovered by filtration. The polymer is then washed with 40 ml of THF. The operation is repeated twice. An orange-coloured powder is then obtained which is used directly in deprotonation reactions. After each use the polymer precursor (3) is reovered by filtration and can again be converted into a supported ylide.

EXAMPLE 2

Use of the Compounds According to the Invention in a C-alkylation Reaction

EXAMPLE 2a

C-benzylation of N-methyl-2-pyrrolidinone

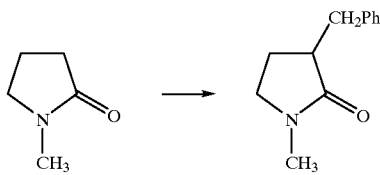

6 mmoles of $(Me_2N)_3P=C(CH_3)_2$ in 27 ml of THF is added to a solution of 5 mmoles of N-methyl-2-pyrrolidinone in 23 ml of THF. The solution is heated at $45°$ C. for 6 hours, then 6 mmoles of benzyl bromide is added and agitation is maintained for an additional hour at $45°$ C. The reaction mixture is left to slowly return to ambient temperature. After extraction with 60 ml of ether, filtration and evaporation of the solvent, the oil obtained is purified on a chromatographic column (eluent: ether/methanol 95/5).

NMR $^1H$ (CDCl$_3$): 2.00 (m, 2H, CH$_2$); 2.63 (m, 2H, CH$_2$—N); 2.79 (s, 3H, CH$_3$—N); 3.10 (m, 3H, CH and CH$_2$Ph); 7.19 (m, 5H, H$_{arom}$).

NMR $^{13}C$ (CDCl$_3$): 23.88 (s, CH$_2$); 29.59 (s, CH$_3$—N); 36.99 (s, CH$_2$); 43.27 (s, CH); 47.39 (s, CH$_2$—N); 126.17, 128.28, 128.88 (s, CH$_{arom}$); 139.29 (s, C$_{ipso}$); 175.72 (s, CO).

EXAMPLE 2b

C-alkylation in Position 3 of Benzodiazepines According to the Following Diagram 1.5 mmoles of ylide $(Me_2N)_3P=C(CH_3)_2$ in 7.5 ml of THF is added, at −78° C., to a solution 1 mmole of compound (B1) in 5 ml of THF. The reaction mixture is agitated for 15 minutes, then 1.5 mmoles of the compound of formula RbX', in which X' represents an atom of halogen and Rb represents an optionally substituted alkyl radical, are added. Agitation is maintained for another 30 minutes. After extraction with 60 ml of ether, filtration and evaporation of the solvent, the oil is purified on a chromatographic column (eluent: pentane/ether 50/50). The compound of formula (B2) is obtained in the form of a powder.

The results obtained according to the value of Ra and Rb are summarized in the table below.

| Ex | Ra | Rb | Yield (%) |
|---|---|---|---|
| $2b_1$ | —$CH_2Ph$ | —$CH_2Ph$ | 38 |
| $2b_2$ | —$CH_2Ph$ | —$CH_2CO_2tBu$ | 42 |
| $2b_3$ | —$CH_2Ph$ | —$CH_3$ | 67 |
| $2b_4$ | —$CH_3$ | —$CH_2Ph$ | 55 |
| $2b_5$ | —$CH_3$ | —$CH_2CO_2tBu$ | 42 |
| $2b_6$ | —$CH_3$ | —$CH_3$ | 43 |
| $2b_7$ | —$CH_2CO_2tBu$ | —$CH_2CO_2tBu$ | 48 |
| $2b_8$ | —$CH_2CO_2tBu$ | —$CH_2Ph$ | 39 |
| $2b_9$ | —$CH_2CO_2tBu$ | —$CH_3$ | 54 |

Characteristics of the Compounds

EXAMPLE $2b_1$ melting point 87° C.

NMR $^1H$ (CDCl$_3$): 3.65 (m, 2H, CH$_2$Ph); 3.87 (m, 1H, CH); 4.68 (d, $^2J_{(HH)}$=15.3 Hz, 1H, N—CH$_2$Ph); 5.68 (d, $^2J_{(HH)}$=15.3 Hz, 1H, N—CH$_2$Ph); 7.20 (m, 18H, H$_{arom}$).

NMR $^{13}C$ (CDCl$_3$): 37.95 (s, CH—CH$_2$Ph); 49.95 (s, N—CH$_2$Ph); 65.27 (s, CH—CH$_2$Ph); 123,92–131.24 (s, CH$_{arom}$); 129.43; 131.99; 136.27; 137.94; 138.99; 140.05 (s, Cq); 167.43; 169.05 (s, CO and CN).

EXAMPLE $2b_2$ melting point 166° C.

NMR $^1H$ (CDCl$_3$): 1.47 (s, 9H, CH$_3$); 3.25 (dd, $^2J_{(HH)}$=16.9 Hz, $^2J(HH)$=7.5 Hz, H$_B$, CH$_2$); 3.43 (dd, $^2J_{(HH)}$=16.9 Hz, $^2J_{(HH)}$=6.5 Hz, H$_B$, CH$_2$); 4.19 (dd, $^3J_{(HH)}$=7.6 Hz, $^3J_{(HH)}$=6.5 Hz, H$_A$, CH); 4.75 (d, $^2J_{(HH)}$=15.5 Hz, H$_A$, N—CH$_2$Ph); 5.60 (d, $^2J_{(HH)}$=15.5 Hz, H$_B$, N—CH$_2$Ph); 6,97–7.43 (m, 13H, H$_{arom}$).

NMR $^{13}C$ (CDCl$_3$):28.14 (s, CH$_3$); 37.80 (s, CH$_2$COOtBu); 50.28 (s, N—CH$_2$Ph); 60.62 (s, CH); 80.70 (s, Cq(CH$_3$)$_3$); 124,01–131.38 (s, CH$_{arom}$); 129.54; 132.11; 136.20; 137.90; 140.31 (s, Cq); 167.50; 169.02; 171.30 (s, CO, CN and COO).

EXAMPLE $2b_3$ melting point 164° C.

NMR $^1H$ (CDCl$_3$): 1.77 (d, $^3J_{(HH)}$=6.4 Hz, 3H, CH$_3$); 3.81 (q, $^3J_{(HH)}$=6.4 Hz, 1H, CH); 4.68 (d, $^2J_{(HH)}$=15.5 Hz, H$_A$, CH$_2$Ph); 5.70 (d, $^2J_{(HH)}$=15.5 Hz, H$_B$, CH$_2$Ph); 6,99–7.42 (m, 13H, H$_{arom}$).

NMR $^{13}C$ (CDCl$_3$): 17.32 (s, CH$_3$); 49.82 (s, CH$_2$Ph); 58.81 (s, CH); 123,94–131.30 (s, CH$_{arom}$); 130.38; 131.07; 136.39; 137.93; 140.20 (s, Cq); 167.16; 170.35 (s, CO and CN).

EXAMPLE $2b_4$ melting point 85° C.

NMR $^1H$ (CDCl$_3$): 3.40 (s, 3H, N—CH$_3$); 3,56–3.77 (m, 3H, CH and CH$_2$Ph); 7,19–7.55 (m, 13H, H$_{arom}$).

NMR $^{13}C$ (CDCl$_3$): 35.28 (s, N—CH$_3$); 38.10 (s, CH$_2$Ph); 65.27 (s, CH); 122,77–131.45 (s, CH$_{arom}$); 129.16; 130.32; 138.15; 139.21; 142.15 (s, Cq); 168.01; 170.05 (s, CO and CN).

EXAMPLE $2b_5$ melting point 141° C.

NMR $^1H$ (CDCl$_3$): 1.45 (s, 9H, CH$_3$); 3.40 (s, 3H, N—CH$_3$); 3.11 (dd, $^2J_{(HH)}$=17.1 Hz, $^2J_{(HH)}$=7.0 Hz, H$_B$, CH$_2$); 3.39 (dd, $^2J_{(HH)}$=17.1 Hz, $^2J_{(HH)}$=6.8 Hz, H$_{B'}$, CH$_2$); 4.07 (dd, $^3J_{(HH)}$=7.0 Hz, $^3J_{(HH)}$=6.8 Hz, H$_A$, CH); 7,25–7.57 (m, 8H, H$_{arom}$).

NMR $^{13}C$ (CDCl$_3$): 28.12 (s, CH$_3$); 35.21 (s, N—CH$_3$); 37.91 (s, CH$_2$); 60.56 (s, CH); 80.59 (s, C$_q$(CH$_3$)$_3$); 122, 83–130.36 (s, CH$_{arom}$); 131.52; 137.97; 139.40; 142.20 (s, C$_q$); 167.20; 169.70; 171.25 (s, CO, CN and COO).

EXAMPLE $2b_6$ melting point 76° C.

NMR $^1H$ (CDCl$_3$): 1.71 (d, $^3J_{(HH)}$=6.5 Hz, 3H, CH$_3$); 3.39 (s, 3H, N—CH$_3$); 3.70 (q, $^3J_{(HH)}$=6.5 Hz, CH); 7,25–7.60 (m, 8H, H$_{arom}$).

NMR $^{13}C$ (CDCl$_3$): 17.43 (s, CH$_3$); 35.15 (s, N—CH$_3$); 58.90 (s, CH); 122,59–130.54 (s, CH$_{arom}$); 129.11; 129.63; 131.38; 138.13 (s, Cq); 166.85; 171.21 (s, CO and CN).

EXAMPLE $2b_7$ melting point 128° C.

NMR $^1H$ (CDCl$_3$): 1.40 (s, 9H, CH$_3$); 1.44 (s, 9H, CH$_3$); 3.14 (dd, $^2J_{(HH)}$=16.9 Hz, $^2J_{(HH)}$=6.8Hz, 1H, H$_B$); 3.43 (dd, $^2J_{(HH)}$=16.9 Hz, $^2J_{(HH)}$=7.0 Hz, 1H, H$_{B'}$); 4.15 (dd, $^3J_{(HH)}$=7.0 Hz, $^3J_{(HH)}$=6.8 Hz, 1H, H$_A$); 4.20 (d, $^2J_{(HH)}$=17.1 Hz, 1H, CH$_2$COOtBu); 4.48 (d, $^2J_{(HH)}$=17.1 Hz, 1H, CH$_2$COOtBu); 7,25–7.60 (m, 8H, H$_{arom}$).

NMR $^{13}$C (CDCl$_3$): 27.90; 28.06 (s, CH$_3$); 7.82 (s, CH$_2$); 50.81 (s, N—CH$_2$); 60.33 (s, CH); 80.61; 82.43 (s, Cq(CH$_3$)$_3$); 123,02–131.64 (s, CH$_{arom}$); 129.89; 130.60; 130.98; 138.08 (s, Cq); 67.39; 167.76; 170.92 (s, CO, CN and COO).

EXAMPLE 2b$_8$ melting point 81° C.

NMR $^1$H (CDCl$_3$): 1.41 (s, 9H, CH$_3$); 3.72 (m, 3H, CH and CH$_2$Ph); 4.40 (d, $^2$J$_{(HH)}$=16.7 Hz, 1H, CH$_2$COOtBu); 4.52 (d, $^2$J$_{(HH)}$=16.7 Hz, 1H, CH$_2$COOtBu); 7,20–7.58 (m, 13H, H$_{arom}$).

NMR $^{13}$C (CDCl$_3$): 27.79 (s, CH$_3$); 37.69 (s, CH$_2$Ph); 50.77 (s, N—CH$_2$COOtBu); 64.72 (s, CH); 82.33 (s, Cq(CH$_3$)$_3$); 122,69–131.45 (s, CH$_{arom}$); 130.68; 131.10; 138.10; 138.91; 141.08 (s, Cq); 167.30; 167.47; 169.49 (s, CO, CN and COO).

EXAMPLE 2b$_9$ melting point 152° C.

NMR $^1$H (CDCl$_3$): 1.41 (s, 9H, CH$_3$); 1.70 (d, $^3$J$_{(HH)}$=6.4 Hz, 3H, CH—CH$_3$); 3.77 (q, $^3$J$_{(HH)}$=6.4 Hz, 1H, CH—CH$_3$); 4.23 (d, $^2$J$_{(HH)}$=17.2 Hz, 1H, CH$_2$COOtBu); 4.51 (d, $^2$J$_{(HH)}$=17.2 Hz, 1H, CH$_2$COOtBu); 7,21–7.60 (m, 8H, H$_{arom}$).

NMR $^{13}$C (CDCl$_3$): 17.16 (s, CH$_3$); 27.81 (s, CH—CH$_3$); 50.65 (s, CH$_2$); 58.46 (s, CH); 82.25 (s, Cq(CH$_3$)$_3$); 122,29–131.37 (s, CH$_{arom}$); 129.41; 130.82; 138.04; 141.18 (s, Cq); 167.04; 167.59; 170.50 (s, CO, CN and COO).

Examples 2a and 2b can also be implemented using a supported ylide as defined in the present invention, and more particularly with a polymer of formula (a) as defined above in which m>1.

EXAMPLE 2c
C-alkylation in Position 3 of Benzodiazepines According to the Following Diagram

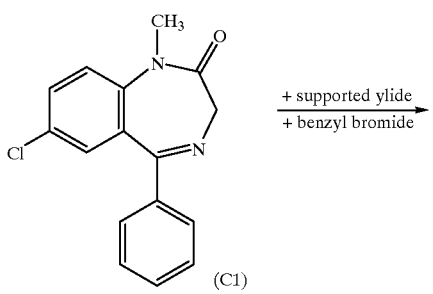

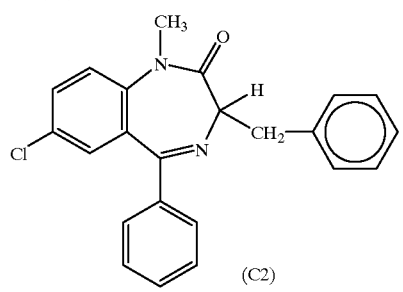

1 g of supported ylide as prepared according to Example 1 is agitated in 20 ml of THF. A solution of 0.7 mmole of compound (C1) in 10 ml of THF is added and the reaction mixture is maintained under agitation for 30 minutes, then 1 mmole of distilled benzyl bromide is added and the reaction mixture is heated at 60° C. for 12 hours. The solution is then separated from the polymers, the solvents are evaporated off under vacuum and compound (C2), identical to compound B2 of Example 2b4, is recovered in the form of an orange powder with a yield of 20%.

EXAMPLE 2d
C-alkylation of Benzodiazepines in Position 3 Using an Aldehyde

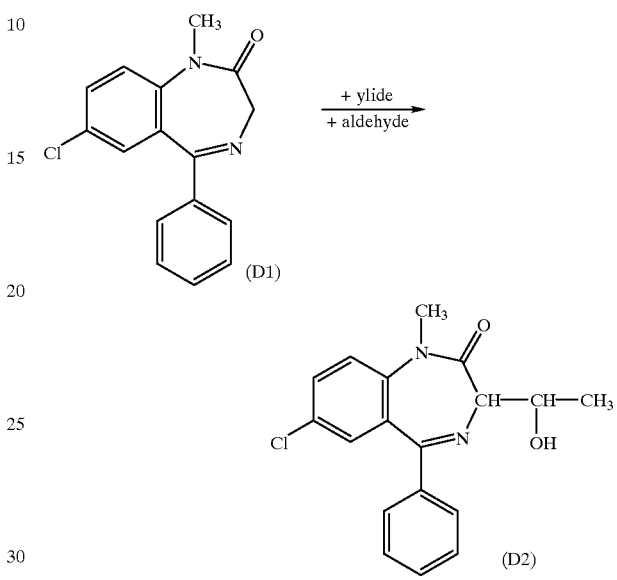

1.5 mmoles of ylide (Me$_2$N)$_3$P═C(CH$_3$)$_2$ in 7.5 ml of THF is added at −78° C., to a solution of 1 mmole of compound (D1) in 5 ml of THF. The reaction mixture is agitated for 15 minutes, then 1.5 mmoles of ethanal is added. Agitation is maintained for another 30 minutes. After extraction with 60 ml of ether, filtration and evaporation of the solvent, the oil is purified on a chromatographic column (eluent pentane/ether 9515). The compound of formula (D2) is obtained in the form of a powder (44%).

EXAMPLE 3
Use of the Compounds According to the Invention in an N-alkylation Reaction

EXAMPLE 3a
N-functionalization of Norvalium

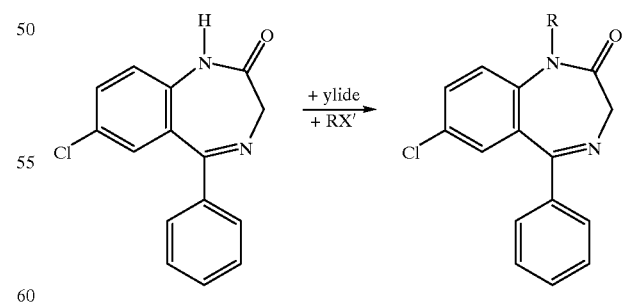

1 g of the supported ylide as prepared according to Example 1 is agitated in 20 ml of THF. A solution of 0.8 mmole of norvalium in 10 ml of THF is added and the mixture is maintained under agitation for 30 minutes. 1 mmol of distilled electrophilic reagent of formula RX' is added in which X' represents a halogen atom and R represents an optionally substituted alkyl radical or SiMe$_3$, and the mixture is left under agitation for 4 hours. The solution is then separated from the polymers, the solvents are evaporated off under vacuum and the oil obtained is taken up in the solvents indicated below. For its part, the polymer is washed and can be re-used later.

| Ex | RX' | Solvent | Yield (%) |
|---|---|---|---|
| 3a$_1$ | Me$_3$SiCl | Pentane | 80 |
| 3a$_2$ | BrCH$_2$CO$_2$tBu | Et$_2$O | 70 |
| 3a$_3$ | PhCH$_2$Br | Et$_2$O | 76 |

EXAMPLE 3a$_1$

NMR $^1$H (CDCl$_3$): 0.30 (s, 9H, CH$_3$); 4.10 (broad s, 2H, CH$_2$); 7.30 (m, 8H, H$_{arom}$).

NMR $^{13}$C (CDCl$_3$): −0.15 (s, CH$_3$); 53.71 (s, CH$_2$); 127,62–128.11 (s, Cq); 129,63–130 CH$_{arom}$); 169.50; 169.52 (s, CO and CN).

EXAMPLE 3a$_2$

NMR $^1$H (CDCl$_3$): 1.40 (s, 9H, CH$_3$); 3.80 (d, $^2$J$_{(HH)}$=10.7 Hz, 1H, CH$_2$); 4.21 (d, $^2$J$_{(HH)}$=15.0 Hz, 1H, CH$_2$COOtBu); 4.45 (d, $^2$J$_{(HH)}$=15.0 Hz, 1H, CH$_2$COOtBu); 4.85 (d, $^2$J$_{(HH)}$=10.7 Hz, 1H, CH$_2$); 7.40 (m, 8H, H$_{arom}$).

NMR $^{13}$C (CDCl$_3$): 27.65 (s, CH$_3$); 51.03 (s, CH$_2$—COOtBu); 51.03 (s, CH$_2$—COOtBu); 55.88 (s, CH$_2$); 83.50 (s, Cq(CH$_3$)$_3$); 123,63–131.98 (s, CH$_{arom}$); 130.23; 130.64; 137.85; 140.56 (s, C$_{ipso}$); 168.30; 170.26; 170.58 (s, CO, COO and CN).

EXAMPLE 3a$_3$

NMR $^1$H (CDCl$_3$): 1.41 (s, 9H, CH$_3$); 3.80 (d, $^2$J$_{(HH)}$=10.5 Hz, 1H, CH$_2$); 4.23 (d, $^2$J$_{(HH)}$=17.2 Hz, 1H, CH$_2$COOtBu); 4.51 (d, $^2$J$_{(HH)}$=17.2 Hz, 1H, CH$_2$COOtBu); 4.96 (d, $^2$J$_{(HH)}$=10.5 Hz, 1H, CH$_2$); 7,21–7.60 (m, 8H, H$_{arom}$).

NMR $^{13}$C (CDCl$_3$): 17.16 (s, CH$_3$); 27.81 (s, CH—CH$_3$); 50.65 (s, CH$_2$); 58.46 (s, CH); 82.25 (s, Cq(CH$_3$)$_3$); 122, 29–131.37 (s, CH$_{arom}$); 129.41; 130.82; 138.04; 141.18 (s, Cq); 167.04; 167.59; 170.50 (s, CO, CN and COO).

EXAMPLE 3b
N-alkylation of Lactames

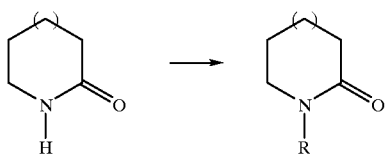

A solution of 3.6 mmoles of (Me$_2$N)$_3$P=C(CH$_3$)$_2$ in 17 ml of THF is added slowly, at 25° C., to a solution of 3 mmoles of substrate in 14 ml of THF. The reaction mixture is agitated at 25° C. for one hour, then 3.6 mmoles of distilled electrophilic reagent of formula RX' in which X' represents a halogen atom and R represents an optionally substituted alkyl radical, are added. Agitation is maintained for 3 more hours. The supernatant solution is separated from the phosphonium salts formed by extraction with 60 ml of ether. After concentration, the oil obtained is purified on a chromatographic column.

| RX' | Eluent | Yield (%) |
|---|---|---|
| CH$_3$I | Et$_2$O/MeOH 85/15 | 60 |
| BrCH$_2$CO$_2$tBu | Et$_2$O | 70 |
| PhCH$_2$Br | Et$_2$O/MeOH 30/70 | 71 |

Characterization of the N-alkylated Lactame:
R=CH$_3$—
NMR $^1$H (CDCl$_3$): 1.82 (m, 4H, CH$_2$—CH$_2$); 2.47 (m, 2H, CH$_2$—CO); 2.98 (s, 3H, CH$_3$—N); 3.31 (m, 2H, CH$_2$—N).
I.R. (CDCl$_3$): 1642 cm$^{-1}$ (CO).
R=tBuOC(O)CH$_2$—
NMR $^1$H (CDCl$_3$): 1.43 (s, 9H, CH$_3$); 1.80 (m, 4H, CH$_2$—CH$_2$); 2.55 (m, 2H, CH$_2$—CO); 3.35 (m, 2H, CH$_2$—N); 4.09 (s, 2H, CH$_2$—COO).
NMR $^{13}$C (CDCl$_3$): 20.44; 22.42 (s, CH$_2$); 27.73 (s, CH$_3$); 31.72 (s, CH$_2$—CO); 49.21; 49.90 (s, CH$_2$—N); 82.49 (s, C(CH$_3$)$_3$); 168.59; 172.37 (s, CO).
R=PhCH$_2$—
NMR $^1$H (CDCl$_3$): 1.70 (m, 4H, CH$_2$—CH$_2$); 2.45 (m, 2H, CH$_2$—CO); 3.14 (m, 2H, CH$_2$—N); 4.53 (s, 2H, CH$_2$Ph); 7.20 (m, 5H, H$_{arom}$).
NMR $^{13}$C (CDCl$_3$): 20.70; 22.60 (s, CH$_2$); 31.89 (s, CH$_2$—CO); 47.08; 49.91 (s, CH$_2$—N); 127.15; 127.57; 128.37 (s, CH$_{arom}$); 136.56 (s, C$_{ipso}$); 170.77 (s, CO)

This example can also be implemented using a supported ylide as defined in the present invention, and more particularly with a polymer of formula (a) as defined above in which m>1.

EXAMPLE 3c
N-benzylation of Peptides

N-t-Boc-L-Leucine and the hydrochloride of the methyl ester of L-phenylalanine, are coupled beforehand in the presence of a BrOP coupling agent in order to obtain the corresponding dipeptide.

4 equivalents of ylide (5.85 mmoles) in 33 ml of THF are added slowly, at 25° C., to a solution of one equivalent of the dipeptide thus obtained (1.60 mmoles) in 9 ml of THF. The reaction mixture is agitated at 25° C. for two hours, then 4 equivalents of benzyl bromide (5.85 mmoles) are added. Agitation is maintained for 3 more hours. The supernatant solution is separated from the phosphonium salts formed by extraction with 60 ml of ether. After concentration, the oil obtained is purified on a silica column (eluent: ether/hexane 50/50).

The monobenzylation product is obtained with a yield of 12% and the dibenzylation product is obtained with a yield of 28%. These compounds were analyzed by gas chromatography coupled with electron impact mass spectrometry.

EXAMPLE 3d
Re-use of a Supported Ylide for the N-functionalization of Norvalium The polymer of Example 2c is washed several times in a dichloromethane/acetonitrile mixture, dried under vacuum and re-used in the N-benzylation reaction of norvalium under conditions as described in Example 3a. The N-benzylated compound is recovered with a yield of 79%, a yield comparable to that obtained in Example 3a$_3$.

What is claimed is:
1. In a process for C-alkylation or N-alkylation, the improvement comprising conducting the C-alkylation or N-alkylation reaction in the presence of a slightly nucleophilic strong base of the following formula

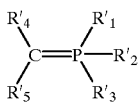
(I')

wherein $R'_1$, $R'_2$ and $R'_3$ are individually selected from the group consisting of alkoxy of 1 to 6 carbon atoms and

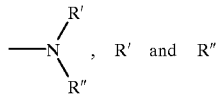, R' and R"

are individually selected from the group consisting of unsubstituted or substituted alkyl of 1 to 6 carbon atoms, alkoxy of 1 to 6 carbon atoms, cycloalkyl of 3 to 10 carbon atoms, aryl and aralkyl of 1 to 6 alkyl carbon atoms, the substituents being selected from the group consisting of halogen, alkyl of 1 to 6 carbon atoms, alkoxy of 1 to 6 carbon atoms, —CN, —NO$_2$ and dialkylamino of 1 to 6 alkyl carbon atoms, the aryl being selected from the group consisting of unsaturated monocyclic and condensed carbocyclic and heterocyclic with at least one heteroatom selected from the group consisting of nitrogen, oxygen and sulfur, $R'_4$ is selected from the group consisting of hydrogen, alkyl of 1 to 6 carbon atoms and alkoxy of 1 to 6 carbon atoms and $R'_5$ is selected from the group consisting of hydrogen, alkyl of 1 to 6 carbon atoms, alkoxy of 1 to 6 carbon atoms and a polymeric support.

2. The process of claim 1 wherein $R'_1$, $R'_2$ and $R'_3$ are individually

.

3. The process of claim 2 wherein $R'_1$, $R'_2$ and $R'_3$ are individually selected from the group consisting of dimethylamino, ethylmethylamino and diethylamino.

4. The process of claim 1 wherein $R'_4$ is hydrogen or alkyl of 1 to 6 carbon atoms.

5. The process of claim 1 wherein $R'_4$ is selected from the group consisting of hydrogen, methyl and ethyl.

6. The process of claim 1 wherein $R'_5$ is alkyl of 1 to 6 carbon atoms or a polymeric support.

7. The process of claim 1 wherein $R'_5$ is a polymeric support selected from the group consisting of a methacrylic polymer, an acrylic polymer and a polystyrenic polymer.

8. The process of claim 7 wherein the polymeric support has the following formula

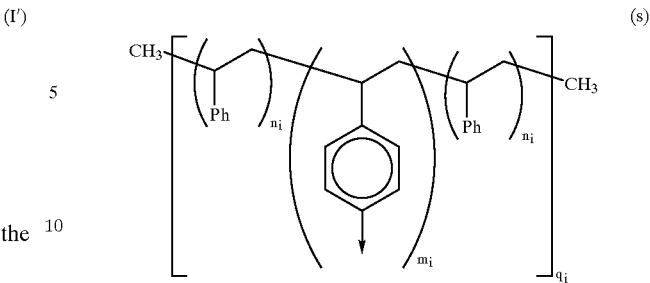

wherein $n_i$, $m_i$, and $q_i$ are integers greater than or equal to 1.

9. The process of claim 8 wherein $m_i$ is 1.

10. The process of claim 1 wherein the base is selected from the group consisting of tris(dimethylamino)-C-dimethylmethylene-phosphorane and styrene/divinylbenzene-tris(dimethylamino)-methylene phosphorane copolymer.

11. The process of claim 1 wherein the reaction is a N-alkylation.

12. The process of claim 11 wherein the N-alkylation is conducted with a member of the group consisting of lactams, succinimides, oligopeptides and benzodiazepines.

13. The process of claim 1 wherein the reaction is a C-alkylation.

14. The process of claim 13 wherein the C-alkylation is conducted with a member selected from the group consisting of lactams, succinimides, Schiff bases and benzodiazepines.

15. A compound of the formula (I)

wherein $R_1$, $R_2$, and $R_3$ are individually selected from the group consisting of alkoxy of 1 to 6 carbon atoms and , R' and R"

are individually selected from the group consisting of unsubstituted or substituted alkyl of 1 to 6 carbon atoms, alkoxy of 1 to 6 carbon atoms, cycloalkyl of 3 to 10 carbon atoms, aryl and aralkyl of 1 to 6 alkyl carbon atoms, the substituents being selected from the group consisting of halogen, alkyl of 1 to 6 carbon atoms, alkoxy of 1 to 6 carbon atoms, —CN, —NO$_2$ and dialkylamino of 1 to 6 alkyl carbon atoms, the aryl being selected from the group consisting of unsaturated monocyclic and condensed carbocyclic and heterocyclic with at least one heteroatom selected from the group consisting of nitrogen, oxygen and sulfur, $R_4$ is selected from the group consisting of hydrogen, alkyl of 1 to 6 carbon atoms and alkoxy of 1 to 6 carbon atoms and $R_5$ is a polymeric support.

16. A compound of claim 15 wherein $R'_1$, $R'_2$ and $R'_3$ are individually

17. A compound of claim 16 wherein

is selected from the group consisting of dimethylamino, ethylmethylamino and diethylamino.

18. A compound of claim 15 wherein $R_4$ is hydrogen.

19. A compound of claim 15 wherein $R_5$ is a polymeric support selected from the group consisting of methacylic polymer, acylic polymer and polystyrene polymer.

20. A compound of claim 19 wherein the polymeric support is a polystyrene of the formula

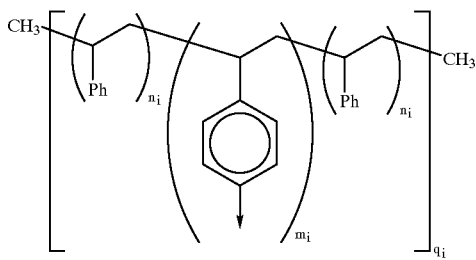

(s)

wherein $n_i$, $m_i$, and $q_i$ are integers of 1 or greater than 1.

21. A process for the preparation of a compound of claim 15 comprising reacting a phosphine of the formula

wherein $R_1$, $R_2$ and $R_3$ are defined as in claim 15 with a compound of the formula

wherein $R_4$ and $R_5$ are defined as in claim 15 and Y is an anion to obtain a compound of the formula

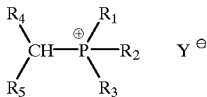

and treating the obtained compound with a strong base to form the compound of claim 15.

22. A compound of the following formula (3)

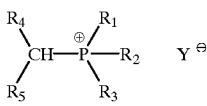

wherein Y is an anion, $R_1$, $R_2$ and $R_3$ are individually selected from the group consisting of alkoxy of 1 to 6 carbon atoms and

$R_4$ is selected from the group consisting of hydrogen, alkyl of 1 to 6 carbon atoms and alkoxy of 1 to 6 carbon atoms, $R_5$ is a polymeric support, R' and R" are individually selected from the group consisting of unsubstituted or substituted alkyl of 1 to 6 carbon atoms, alkoxy of 1 to 6 carbon atoms, cycloalkyl of 3 to 10 carbon atoms, aralkyl of 1 to 6 alkyl carbon atoms and aryl, the substituents being at least one member of the group consisting of halogen, alkyl of 1 to 6 carbon atoms, alkoxy of 1 to 6 carbon atoms, —CN, —$NO_2$ and dialkylamino of 1 to 6 alkyl carbon atoms.

* * * * *